United States Patent
Bernstein et al.

[11] Patent Number: 5,824,268
[45] Date of Patent: Oct. 20, 1998

[54] RAPID SELF-CONTAINED ASSAY FORMAT

[75] Inventors: David Bernstein, Eldersburg; Mary Ann Childs, Baltimore, both of Md.; William Trainor, Hillsboro Beach, Fla.; Majorie Wier; Erick Gray, both of Columbia, Md.

[73] Assignee: Universal Health Watch, Inc., Columbia, Md.

[21] Appl. No.: 950,331

[22] Filed: Oct. 14, 1997

Related U.S. Application Data

[63] Continuation of Ser. No. 444,721, May 19, 1995, abandoned.

[51] Int. Cl.⁶ ................................................ G01N 33/558
[52] U.S. Cl. ........................ 422/56; 422/58; 422/61; 435/7.1; 435/7.92; 435/7.94; 435/970; 436/530
[58] Field of Search ........................ 422/56, 58, 61; 436/180, 530, 528, 531, 161; 435/7.1, 969, 970, 975, 7.94, 7.92

[56] References Cited

U.S. PATENT DOCUMENTS

| | | |
|---|---|---|
| 3,893,808 | 7/1975 | Campbell . |
| 3,895,914 | 7/1975 | Alberty et al. . |
| 4,168,146 | 9/1979 | Grubb et al. . |
| 4,298,688 | 11/1981 | Kallies ........................................ 435/14 |
| 4,361,537 | 11/1982 | Deutsch et al. ............................ 422/56 |
| 4,435,504 | 3/1984 | Zuk et al. . |
| 4,452,901 | 6/1984 | Gordon et al. ............................ 436/506 |
| 4,517,288 | 5/1985 | Giegel et al. . |
| 4,562,043 | 12/1985 | Mennen et al. ............................ 422/56 |
| 4,855,240 | 8/1989 | Rosentein et al. ...................... 436/514 |
| 4,891,313 | 1/1990 | Berger et al. ............................. 436/518 |
| 4,943,522 | 7/1990 | Eisinger et al. ........................... 422/58 |
| 4,960,691 | 10/1990 | Gordon et al. ............................... 435/6 |
| 4,981,786 | 1/1991 | Dafforn ..................................... 422/56 |
| 5,079,142 | 1/1992 | Coleman et al. ....................... 435/7.92 |
| 5,308,580 | 5/1994 | Clark ......................................... 422/61 |
| 5,468,648 | 11/1995 | Chandler ................................. 436/518 |
| 5,500,187 | 3/1996 | Deoms et al. ............................. 422/58 |

*Primary Examiner*—Jan Ludlow
*Attorney, Agent, or Firm*—Foley & Lardner

[57] ABSTRACT

A test strip, a device incorporating the test strip and a method for use of the test strip within the device detecting an analyte in a solution or bodily fluid are disclosed. The test strip was three zones, a reaction zone coated with a substance that binds the analyte, a sample zone with a region for addition of the sample of solution or fluid, and a detection region zone with a region coated with detection reagent. An absorbent pad underlies the reaction zone. The reaction zone is a small membrane and is physically in contact on its upper surface with both the sample zone and the detection zone. The test strip is incorporated into a device which includes a sample collection/transferring device, a housing for holding the test strip, and a container for holding solvent solutions at both outer ends of the test strip such that the solvent solutions can come into contact with the outer ends of the test strip when pressure is applied to the ends. The method involves placing a sample onto the strip using the sample collection/transferring device, causing solvent solutions to come into contact with the sample and detection membranes, and observing the test results. The resulting orthogonal buffer flow is an improvement over current methods because it reduces the number of steps and the time required for performance of a sequential assay.

16 Claims, 2 Drawing Sheets

RAPID SELF-CONTAINED ASSAY FORMAT

This application is a continuation of application Ser. No. 08/444,721, filed May 19, 1995 now abandoned.

BACKGROUND

In many situations including rural areas, public health clinics, developing nations where tests for detection of a substance in blood, plasma or other secretion such as saliva or fluid such as urine must be performed without aid of complicated instruments or in situation where non trained or non medical people will be using such a test, it is necessary to design assays that are accurate, easy to perform, rapid, and with a minimum number of steps. Reduction of the number of steps and the need for large quantities of reagents is also important in reducing the costs of these types of test.

Assays based on specific binding reactions have been used for detecting a wide variety of components such as drugs, hormones, enzymes, proteins, antibodies, and infectious agents in various biological fluids and tissue samples. In general, the assays consist of an analyte, a binding substnace for the analyte, and a detection reagent. Immunological assays involve reactions between immunoglobulins (antibodies) which are capable of binding with specific antigenic determinants of various compounds and materials (antigens). Other types of reactions include binding between avidin and biotin, protein A and immunoglobulins, lectins and sugar moieties and the like.

The detection reagent is necessary because the results of specific binding reactions are frequently not directly observable. A variety of detection reagents have been devised for determining the presence of a reaction. Detection reagents have involved well known techniques including radiolabelling and the use of chromophores, fluorophores and enzyme labels. Radiolabels, chromophores and fluorophores may be detected by use of radiation detectors, spectrophotometers or the naked eye. Where members of a specific binding pair are tagged with an enzyme label, their presence may be detected by the enzymatic activation of a reaction system wherein a compound such as a dyestuff, is activated to produce a detectable signal.

Immunological assays are of three general types. In competitive binding assays, labelled reagents and unlabelled analyte compounds compete for binding sites on a binding material. After an incubation period, unbound materials are washed off and the amount of labelled reagent bound to the site is compared to reference amounts for determination of the analyte concentration in the sample solution. A second type of immunological assay is known as a sandwich assay and generally involves contacting an analyte sample solution to a surface comprising a first binding material immunologically specific for that analyte. A second solution comprising a labelled binding material of the same type (antigen or antibody) as the first binding material is then added to the assay. The labelled binding material will bind to any analyte which is bound to the first binding material. The assay system is then subjected to a wash step to remove labelled binding material which failed to bind with the analyte and the amount of labelled material remaining is ordinarily proportional to the amount of bound analyte.

A third type of immunological assay technique involves agglutination reaction techniques and is exemplified by well-known assays for blood antigens and serum types. Immunological cross-reactivity between antibodies within serum and antigens presented on red blood cell surfaces is indicated by the formation of a three dimensional cross-linked netowrk of red blood cells and antibodies. The agglutination of the serum/red blood cell mixture results in the formation of a pellet which can be visible to the naked eye.

These various assay procedures were originally performed according to liquid phase immunochemistry techniques wherein enzymes and radiolabelled reactions were carried out in liquid solution in apparatus such as microtiter plates. More recently, techniques and procedures have been adapted for carrying out "solid" phase assays wherein enzymatic and immunological reactions are carried out in solution on damp porous solid substrates.

These types of assays generally designated immunochromatographic immunoassays can be developed in any number of formats employing prinicpals of competitive, sandwich, or agglutination types of assays. They can also involve either flow acrost or flow along the membrane. In general, the sandwich assays have the greatest utility for detection of large protein analytes or antibodies. The flow acrost type of assays have been used most extensively in sandwich type assays. A particular limitation of current immunochromatographic assay techniques is the requirement of numerous addition and wash steps. These steps, required to prevent undesired cross-reactions and remove excess reagents and interfering substances, complicate the procedure and effectively limit the type and level of sophistication of analytical procedures that may be carried out. Elimination or reduction of the number of washing and addition steps which must be carried out by technical personnel will not only reduce time and expense of conducting assays and analyzing assay result analysis. For these reasons, new systems involving solid phase assay devices requiring a minimum number of additions and washing steps are highly desired.

Many immunochromatographic sandwich immunoassay procedures have been developed which employ a porous surface and microparticles such as polystyrene latex spheres, natural or synthetic dyes, or metal sol particles such as colloidal gold, as visual labels which in the presence of a suitable solvent can diffuse through or across a porous surface. One member of a binding pair is adsorbed to the surface of such particles either through covalent or noncovalent attachment. The porous surface is generally a flat sheet and is usually comprised of either nylon, nitrocellulose, glass fiber, or the like. In a typical immunochromatographic format a region or small area of the porous surface becomes a solid phase capturing surface by immobilizing a member of a binding pair directly onto the surface of a porous membrane or by indirectly attaching the member onto capture particles (i.e., latex, glass,) which are immobilized on the surface of a porous membrane. Direct immobilization of the binding pair to a porous membrane or capture particles occur through electrostatic interaction, (i.e., differences in ionic charge), hydrophobic interaction, or covalent binding. Where capture particles are used the immobilization of capture particles to porous membranse can also occur through the same phenomena or through size exclusion preventing migration of the particles through the pores or fibers of the membrane.

In a typical noncompetitive immunochromatographic assay, a test sample of a biological fluid such as blood, serum, plasma, saliva, urine, etc. must be in a sufficient volume and concentration of analyte to allow for sufficient interaction to occur between the analyte of interest, the labeled particles and the capturing solid phase. In order to increase the reaction kinetics, the concentration of particle labeled member of a binding pair and theconcentration of binding pair at the surface of the porous membrane or capturing particles is optimized to produce as much specific binding as possible and at the same time minimize any nonspecific binding. The concentration of the particle labeled member must be of a concentration that does not produice prozone phenomena throughout the range of analyte concentrations that are of interest.

Immunochromatographic assays can be in the form of strips or layers of porous materials employing a hydrophobic support (i.e., Mylar, polystyrene. polypropylene, glass, etc.) wherein the porous surface either fixed either directly or indirectly with a binder such as glue (i.e., rubber cement) to the support. Hydrophobic supports and housings can be employed to reduce evaporation of the fluid phase while the immunoreactants are being brought into contact with each other.

A major obstacle in performing sandwich immunochromatographic assays has been the need to balance the concentrations of a labeled binding member and a capturing binding member throughout the range of analyte of clinical interest. Due to prozone phenomena, assays have employed sequential addition of immunoreactants with appropriate washing steps to remove unbound analyte and any unbound particle labeled member or employ a dilution of test sample so as not to overwhelm the concentration of the particle labeled binding member. Dilution of the analyte sample can reduce sensitivity of an assay and need for washing steps reduce the speed and ease of an assay.

Throughout the world, diagnosis of disease or detection of pathogenic agents in the field can result in a shorter time to take remedial or therapeutic actions. In order to make testing more-widely available, there is a need to use as simple methods as possible for both ease of use and ease of interpreting test results. A simple test device wherein all the reagents, including liquid phase solvents, buffers, etc., necessary to perform the assay are incorporated and requiring only the addition of test sample would be highly advantageous in such settings.

DESCRIPTION OF PRIOR ART

U.S. Pat. No. 4,168,146 to Grubb, et al., discloses the use of test strips for carrying out assertedly "solid phase" sandwich-type immunoassays. The strips are formed of bibulous carrier materials to which antibodies have been attached by adsorption, absorption or covalent bonding. Preferred test strip materials include celulose fibre-containing materials such as filter paper, ion exchange paper and chromatographic paper. Also disclosed are uses of materials such as cellulose thin-layer chromatography discs, cellulose acetate discs, starch and three dimensional crosslinked materials such as Sephadex (Pharmacia Fine Chemicals, Uppsala Sweden). Immunoassays are carried out by wetting the test strips with measured amounts of an aqueous solution containing the suspected antigen. Antigen molecules within the test solution migrate by capillary action throughout the test strip, but because the bound antibodies retard the migration of the antigens for which they are specific, the extent of migration of the antigen molecules over a fixed time period is related as a function of the antigen concentration in the test solution. The antigen-containing areas of the diagnostic device are then indicated by the addition of labelled antibodies.

U.S. Pat. No. 4,517,288 to Giegel, et al., discloses methods for conducting solid phase immunoassays on inert porous materials. The patent discloses immunologically immobilizing a binding material within a specified zone of the porous material and applying the analyte to the zone containing the immobilized binding material. A labelled indicator material which will bind with the analyte is then applied to the zone where it will become immobilized in an amount correlated to the amount of analyte in the zone. A solvent is then applied to the center of the zone to chromatographically remove the unbound labelled indicator from the zone so that the amount of labelled indicator remaining in the zone may then be measured.

Deutsch, et al., U.S. Pat. No. 4,361,537 discloses test devices for the performance of specific binding asays comprising a strip capable of transporting a developing liquid by capillarity which has a first zone for receiving a sample, a second zone impregnated with a first reagent capable of being transported by the developing liquid and a third zone impregtnated with a third reagent. In addition, the devices comprise a measuring zone and a retarding element which may be either the second reagent or the material of the strip. The first reagent is capable of reacting with one of the group consisting of (1) the sample, (2) the sample and the second reagent, or (3) the second reagent in competition with the sample, to form a product in an amount dependent on the characteristic being determined. A sample is contacted with the first zone and the strip is then dipped into the developing liquid to bring about transport of the sample and the first reagent to form the reaction product. The retarding element slows transport of either the product or the first reagent (the moving reagent) to spacially separate the two and the amount of the moving element is then measured at the measurement location.

U.S. Pat. No. 4,435,504 to Zuk, et al., discloses a chromatographic immunoassay wherin the distance at which a border is formed from one end of the chromatograph is indicative of the quantity of analyte present in a sample. The analyte which is a member of a specific binding pair is immunochromatographed on a bibulous carrier to which its binding partner is nondiffusively bound and a variety of protocols are utilized to provide for delineation between the region to which the analyte is bound and the region free of analyte. According to one protocol, the analyte is chromatographed in the presence or absence of a labelled binding conjugate where the label is a member of an enzymatic signal producing system which includes one or more enzymes. If the labelled conjugate is not chromatographed with the analyte, the conjugate is applied to the chromatograph where it will bind to the chromatograph in proportion to the amount of analyte present. Similarly, if the labelled conjugate is chromatographed with the analyte, then the conjugate will bind to the analyte in proportion to the amount of analyte present at that position. The labelled conjugate can be an enzyme member of a signal producing system which can include chromorphores, phosphors, fluorescers and chemiluminescers as well a coupled enzymatic signal systems. Where a coupled enzyme system is utilized, a second enzyme capable of reacting with the product of the first may be chromatographed with the analytes solution or may be added to the test strip after chromatography of the analyte.

Europen Patent Application No. 164,194 (published Dec. 11, 1985) disclosed improvements on the methods of Zuk, et al., in that transported chromatographic materials have substantially the same rate of traversal along the longitudinal edge of the of the chromatographic strip as along the body of the strip. This allows the chromatographic transport front to remain substantially flat rather than concave.

U.S. Pat. No. 4,452,901 to Gordon discloses the use of porous nitrocellulose supports for immobilization of proteins. It is disclosed that such nitrocellulose sheets may be utilized in immunoassay procedures if the residual binding capactiies of the nitrocellulose sheets are saturated by blocking treatment with one or more types of proteins, different from those immobilized and not cross-reactive with any of the antibodies subsequently used in the assay.

Gordon, EPO Application 63,810, published Nov. 3, 1982, further relates to devices for conducting immunological assays. The devices consist of a porous solid support containing a preselected array of delimited adsorption areas of antigens, antibodies or both, wherein residual adsorption sites on the substrate are saturated by protein blocking agents such as bovine serum albumin which do not cross-react with the antigens or antibodies employed in the assay. The porous supports are disclosed to have sufficient surface porosity to allow access by antibodies and surface affinity suitable for binding antigens. Such supports are disclosed to be selectable from a variety of natural and synthetic polymers and derivatives but are preferably nitrocellulose sheets 0.1 mm thick with pore size between about 0.15 $\mu$m and about 15 $\mu$m. Antigens or antibodies are applied to the porous solid support by agents. Assays for detection of unknown antigens or antibodies are then carried out through use of labelled antibodies which may also be anti-immunoglobulin antibodies. Results of single or multiple assays are determined by detection of the labelled antibodies.

Gordon, et al, U.S. Pat. No. 4,960,691, further disloses a test strip for analysis of analytes such as antigens, antibodies or polynucleotides which consists of a chromatographic strip and a solvent. The strip has three zones, a sample zone, a label zone, and a detection zone. The reagents are selected and placed on the strip so that there is a sequential arrival at a detection site of first analyte, then a labeled reagent. Multiple and single pathways for accomplishing sequential steps including washing away of unreacted materials is accomplished.

Campbell, U.S. Pat. No. 3,893,808 discloses a test strip for the detection of lead contamination in unleaded motor fuels. The test strip comprises a paper strip having three zones. The first zone is impregnated with iodine, while the second zone is treated with a mixture of iodine and potassium iodide. A sample of motor fuel to be tested is applied to the strip and is transported by means of capillary action through the first and second zones to the third zone to which a dithizone indicator solution is then added. Any organic lead present in the motor fuel is converted to inorganic lead iodide on the surface of the strip and this is detected by reaction with the dithizone indicator to form a lead dithizonate complex with a characteristic color.

Alberty, et al., U.S. Pat. No. 3,895,914 discloses a test strip for the detection of barbituric acid and barbituric acid derivatives in a biological fluid. The strip comprises a bibulous paper strip having three zones. The first zone is impregnated with acid in order to acidify sample fluids applied thereto. The second zone is impregnated with alkaline buffered mercuric acetate capable of reacting to form a barbituatemercury complex. The third zone is impregnated with a mercury indicating compound such as diphenyl carbazone. A sample of fluid to be tested is applied to the first zone and the strip is dipped in solvent. Barbiturates present in the sample will react to form a barbiturate-mercury complex which will be transported to the third zone and will react with the mercury indicating compound.

Kallies, U.S. Pat. No. 4,298,688, discloses an assay device for the determination of glucose levels in biological fluids. The device comprises a paper test strip demarcated into a mearuring zone which may be untreated, a reaction zone containing glucose oxidase, and a detection zone containing peroxidase and indicator substances such as o-tolidine and Orasol yellow. The material to be assayed is allowed to diffuse through the measuring zone to the reaction zone, wherein any glucose will react with the glucose oxidase, and then to the detection zone wherein a color reaction will take place, the degree of which depends on the extent of reaction carried out in the reaction zone. Water may be used to assist the diffusion of the test materials through the device and the test strip may also be enclosed within a glass capillary tube.

In all these previous disclosures, there are requirements for multiple additions of solvent or mixture of solvent and sample prior to addition of the mixture to the test strip. None of these previous disclosures discusses an orthogonal arrangement with an underlying pad for the adsorption of excess sample, reagents and wash despite the fact that this arrangement reduces the number of steps to be performed, improves the ability of the test to detect the analyte and decreases the time of the test.

SUMMARY OF THE INVENTION.

The strip, device, and method of the current invention are useful for determining the presence of an analyte in a sample with a minimum number of steps and within a short time period. The test device is a series of bilbulous strips comprised of a reaction zone having bound a member of the binding pair on the surface of a porous membrane, a sample zone having a place for placement of the sample by the sample collecting/transferring part of the device onto the surface of a porous membrane, and a detection reagent zone having an area for either direct or indirect placement of detection reagent onto the surface of a porous membrane. The sample zone and the detection reagent zone are both bibulous materials (porous membranes) spacially separated from each other, but each in physical contact with the upper surface of the porous membrane containing said reaction zone. The bibulous materials comprising the sample zone and the reaction zone are used to bring solvent and reagents in contact with the reaction zone in an appropriate sequence. The test device further involves an absorbant pad that is located so that it makes contact with the lower surface of the porous membrane containing the reaction zone. The device encompasses the strip and in addition, encompasses a means for both collecting and adding a sample in a discrete fashion to the test strip device. The sample collecting part of the device is comprised of a plastic, absorbant, or combination thereof. The sample collecting/transferring means can be pretreated with suitable binders, anticoagulants, buffers etc., to enhance penetration of the analyte into the test device while reducing any potential inhibitors or interferring substances (i.e., red blood cells, debris, etc.). In addition, the device contains buffer reservoirs continguous with the ends of the sample zone and the detection reagent zone distal to the reaction zone and separated from these reservoirs by thin liquid impermeable membranes that can be rendered liquid permeable through pressure.

In the method, a sample is collected using the sample collection/transferring part of the device and added to the sample zone. Buffer is added to the ends of the sample zone and the detection reagent zone distal to the reaction zone either manually or by rupturing the membranes on top of the resevoirs at the two ends of the device through pressure. The buffers traverse the sample zone and the detection zone in opposing directions by capillary action causing the sample on one side and the detection reagent on the other side to enter into the reaction zone. The size of the strips, placements of sample and detection reagent and choice of buffers are all selected to insure that the sample reaches the reaction zone first and excess sample is washed through into the underlying absorbant pad before the detection reagent reaches the reaction zone. After a period of less than 10 minutes, the reaction zone is examined for the presence of detectable detection reagent.

A significant improvement in this strip is related to the flow of the sample and the detection reagent in opposite directions towards the detection area. A result of this orthogonal flow is that the potential for prior reaction of sample and detection reagent components is eliminated so that there is no chance for prozoning effects. The use of different materials for the reaction zone and the sample and detection reagent zone allow for more precise control over the conditions in each zone. The reaction zone can be made of a material that is particularly good for binding while the sample and detection reagent zones are good for solvent transport.

The device containing the strip is an improvement over current devices because all materials are contained within the test device insuring accurate performance of the test with the most minimal of instructions.

The advantage of the method is that the presence of an analyte can be determined in a solution in a sequential form of immunoassay, i.e., the excess sample can be washed away before the detection reagent is added, in a format that does not require multiple steps or reagent additions. Because all reagents are flowing simultaneously, the assay time will be shorter for any given result.

BRIEF DESCRIPTION OF THE DRAWINGS

FIG. 1a shows a side view of the strip while FIG. 1b shows a top view of the strip.

DETAILED DESCRIPTION OF THE INVENTION

Figure 1A:
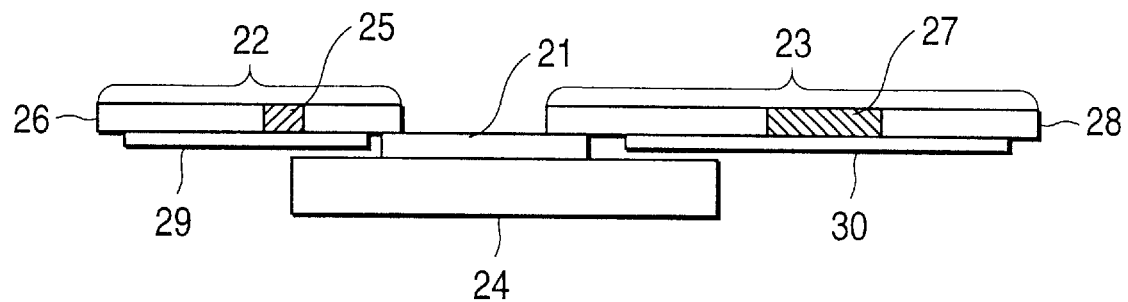
FIG. 1a and 1b present the component parts of the immunochromatographic strip aspect of the invention.

As discussed above, this invention concerns a test strip, a device, and a method for collecting, transferring, and testing a sample for the presence of an analyte with a minimum number of steps and in a contained system. Before proceeding with a detailed description of the invention certain terms will be defined.

Analyte—the compound or composition to be measured that is capable of binding specifically to an antigen, an antibody, or a receptor. Examples of analytes include monovalent analytes such as drugs, hormones, pesticides, organochemicals and the like as well as polyvalent analytes such as polypeptides and proteins including immunoglobulins, polysaccharides, nucleic acids, and combinations thereof. Such combinations or assemblages include bacteria, viruses, chromosomes, genes, mitochondria, nuclei, cell membranes and the like.

Antibody—an iummunoglobulin or derivative or fragment thereof having an area on the surface or in a cavity which specifically binds to and is thereby defined as complementary with a particular spatial and polar organization of another molecule. The antibody can be monoclonal or polyclonal and can be prepared by techniques that are well known in the art such as immunization of a host and collection of sera or hybrid cell line technology.

Analyte binding reagent—any compound or composition capable of recognizing a particular spatial and polar organization of an analyte. In the case of an analyte which is a specific immunoglobulin species the analyte binding reagent may be the specific protein or eptitope recognized by the immunoglobulin. Other types of analyte binding reagents include include naturally occuring receptors, antibodies, enzymes, Fab fragments, lectins, nucleic acids, avidin, protein A, complement component Clq, and the like.

Detection reagent—a material that is an analyte binding reagent that is labeled with a substance capable of being detected. For an assay for specific forms of antibody, a preferred detection reagent would be protein A labeled with colloidal gold. Other detection reagents for antibody as an analyte would include an antibody directed to the antibody that is the analyte, e.g., goat antihuman IgG labeled with gold for detection of human antibody. In another embodiment the analyte binding reagent may be conjugated to hapten such as biotin and the detection reagnet may be be specific for such hapten such as, e.g., antibiotin or avidin.

A label may be any molecule bound or conjugated to an analyte binding reagent that is can produce a signal. In the subject invention, the label is capable of spontaneously producing a detectible signal without any additional reagents and will be detectable by visual means. The preferred embodiment is colloidal gold as a label. Other embodiments could include other colloidal metals, colored particles, liposomes filled with a colored substance. Many such substances will be known to those skilled in the art.

Bibulous material—a porous material having pores of at least $0.1\mu$, preferably at least $1.0\mu$, which is susceptible to traversal by an aqueous medium in response to capillary force. Such materials are generally hydrophilic or are capable of being rendered hydrophilic and include inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked destran, agarose, polyacrylate, etc.; either used by themselves or in conjunction with other materials; ceramic materials; and the like. The bibulous material can be attached to a support. On the other hand, the bibulous material may provide its own support. The bibulous material may be polyfunctional or be capable of being polyfunctionalized to permit covalent bonding of receptiors or antibodies as well as to permit bonding of other compounds which form a part of the signal producing system.

Binding of analyte binding reagents and detection reagents to the bibulous material may be accomplished by well-known techniques, commonly available in the literature. See, for example, "Immolbilized Enzymes," Ichiro Chibata Halsted Press, New York (1978) and Cuatrecasas, J. Bio. Chem., 245:3059 (1970).

The piece of bibulous material can be a single structure such as a sheet cut into strips or it can be several strips or particulate material bound to a support or solid surface such as found, for example, in thin-layer chromatography.

The support for the bibulous material where a support is desired or necessary will normally be water insoluble, non-porous, and rigid and usually will be of the same length and width as the bibulous strip but may be larger or smaller. A wide variety of organic and inorganic materials, both natural and synthetic, and combinations thereof, may be employed provided only that the support does not interfere with the capillary action of the strip, or non-specifically bind assay components, or interfere with the signal producing system. Illustrative polymers include polyethylene, polyporpylene, poly(4-methylbutene), polystyrene, polymethacrylate, poly(ethylene terephthalate), nylon, poly (vinyl butyrate), glass ceramics, metals, and the like.

The absorbent pad may be any hydrophilic bibulous material such as paper, sponge, felt, porous polymers and the like.

The preferred embodiment is a sandwich assay. Those skilled in the art can deduce the application of the present invention in competitive or noncompetitive assays for analytes of suitable interest including haptens, antigens, and antibodies. Detailed description of each of the figures follows and the method of the preferred embodiment follows.

Figure 1B:
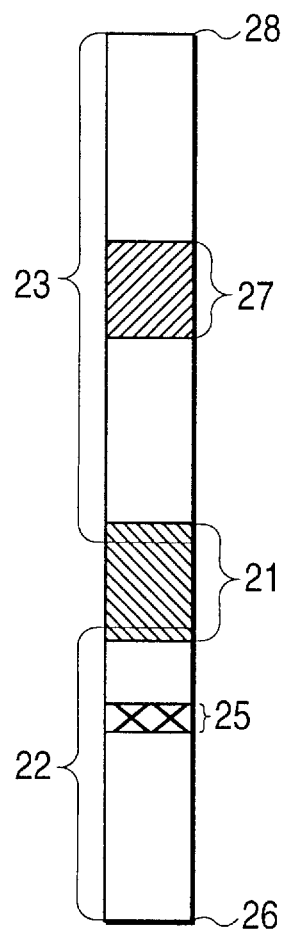

The test strip consists of three discrete zones, a reaction zone, a sample zone and a detection reagent zone. The test strip shown in FIG. 1 is comprised of a reaction zone (21), a sample membrane (22), a detection membrane (23) and an absorbent pad (24). The reaction zone is a membrane consisting of a biblulous material with pore size in the range of 0.2–5 µm but preferably of 0.45 µm and in the preferred embodiment is constructed of nitrocellulose. Analyte binding substance is non-diffusively bound to this membrane preferably in a line in the central part of the membrane. An additonal substance that will bind another material in all samples of the type to be used in conjunction with the test may also be bound in the analyte detection region as an internal control for the completion of the assay. The reaction zone membrane is smaller in length than the sample and detection reagent membrane strips and in the preferred embodiment is approximately 10 mm×10 mm in size although a variety of sizes and shapes are possible.

The sample membrane (22) is in physical contact with a portion of the reaction zone on its upper surface such that liquid flowing through the sample membrane can freely move from the sample membrane through the reaction zone. The overlap of the two membranes for the two zones must be sufficient to insure good solvent transfer, but must not obscure the area where the analyte bininding substance is coated on the reaction zone. The sample membrane is a bilbulous material preferably of a larger pore size than the reaction zone membrane. In the preferred embodiment the sample membrane is 30 mm long by 10 mm wide and is composed of nitrocellulose with 5.0 micron pores although a variety of materials can be used for this membrane. The sample membrane has a site for the addition of sample (25). In the test method, buffer is added to the end of the sample membrane distal to the reaction zone (27). The site for sample addition (25) is placed so that the sample will reach the reaction zone just ahead of the buffer front from the sample solvent solution added at the end of the sample membrane. On its lower surface the sample membrane will be in close contact with a liquid impremeable material such as mylar or plastic (29) except in the area in which it contacts the reaction zone.

The detection reagent membrane (23) is also in physical contact with a portion of the reaction zone on its upper surface such that liquid flowing through the detection reagent membrane can freely move from the sample membrane through the reaction zone. In the preferred embodiment, the detection reagent membrane is 40 mm long by 10 mm wide and is composed of nitrocellulose with 5.0 micron pores although a variety of materials can be used for this membrane. The detection reagent membrane has an area on which the detection reagent is coated. In the test method, buffer is added to the end of the sample membrane distal to the reaction zone (28). The detection reagent must be placed on the membrane (26) such that the detection reagent will reach the reaction zone after the sample has reached the zone and sufficient sample solvent has flowed through the reaction zone to remove unbound sample. The detection reagent may be bound onto the detection membrane in the presence of a variety of substances including sugars or other proteins that may improve the rehydration of the detection reagent. On its lower surface the detection reagent membrane will be in close contact with a liquid impremeable material (30) such as mylar or plastic expect in the area in which it contacts the reaction zone and potentially at the end distal to the reaction zone.

An absorbent pad reservoir is placed against the reaction zone on its under surface (24) and is of sufficent size and composition so that it is capable of absorbing excess sample, detection reagent, and solvent. The absorbent is physically removed from the sample membrane and the detection reagent membrane by liquid impremeable materials that underlie these membranes.

The solvents that are added to the distal ends of the sample membrane and detection reagent strips are composed such that they will promote the movement of the critical components of the reagents along the strips and will be composed of a buffered salt solution and a detergent. In the preferred embodiment, the solvent for both strips is phosphate buffered saline containing 0.1% Triton-X. The solvents may be different for the two membranes, may contain a variety of detergents and other materials such as polyethylene glycol that can enhance reactions.

In general, the test strip will be incorporated into a test device with means for sample collection/transferring to the strip, means for holding the strip in place, means for maintaining buffer reservoirs that can be released by pressure onto the ends of the membranes that constitute the sample and detection reagent zones.

Figure 2:
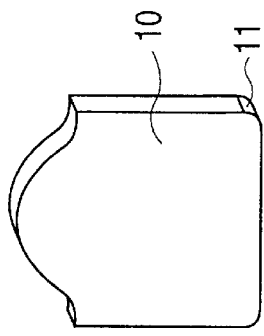
FIG. 2 presents the sample collecting/transferring device.

The first part of the device is a sample collection/transferring means as shown in FIG. 2. The sample collection/transferring means consists of a physical end for holding the device (10) and an absorbent means for taking up the sample (11). The device is configured so that its width is essentially that of the test strip so that the sample is delivered to the test strip in a discrete line. In the preferred embodiment of the invention, the sample is a whole blood sample resulting from a fingerstick. The absorbent material is a membrane that excludes red blood cells and is further treated with a buffer containing 0.1 M ammonium chloride to lyse red blood cells so that the sample delivered onto the test strip is essentially plasma with little contamination from whole red blood cells. In the preferred embodiment, the test strip of FIG. 2 is encased in a plastic holder and the sample collection/transferring device is constructed so that it locks into a place in the holder making contact with the test strip.

Figure 3:
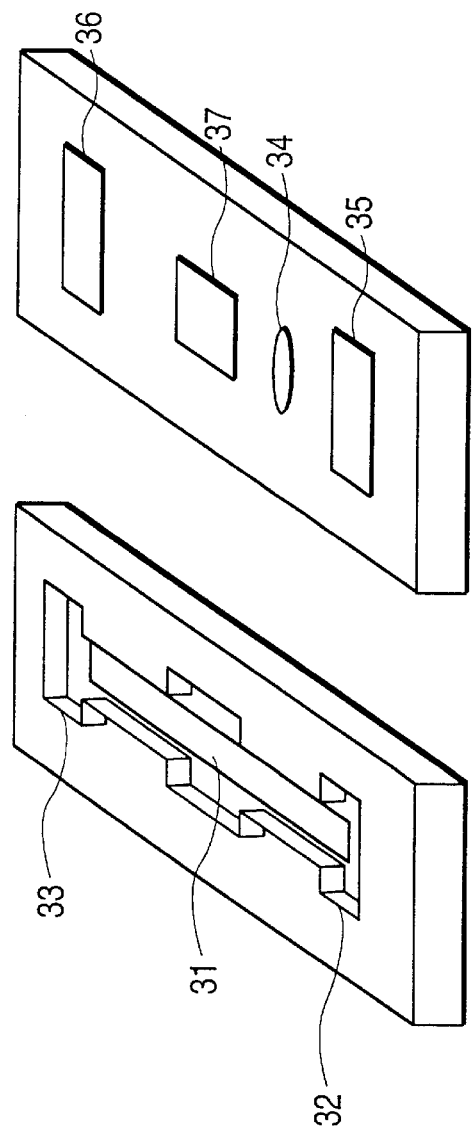
FIG. 3 presents the test device including the placement of the strip within the device.

FIG. 3 shows the plastic device into which the sample collection/transferring device is placed. The device comprises an area for placement of the strip with its three zones (31), a buffer resevoir for the solvent that will flow through the sample strip (32), and a buffer reservoir for the solvent that will flow through the detection reagent strip(33).

The top piece of the device is of impremeable plastic and has an orifice (34) that is cut to be the size of the sample collecting/transferring device so that once the sample collecting/transferring device is placed in this orifice, the lower edge of the sample collecting/transferring device makes contact with the strip. The top of the device also has areas where pressure can be applied to release the solvents to flow onto the membrane strips. Pressure on the lower contact point (35) brings the solvent reservoir underlying this point into contact with the sample membrane. Pressure on the upper contact point (36) brings the solvent reservoir underlying this point into contact with the detection reagent membrane. The device also has a window for reading the results of the test (37).

Samples will be tested for the presence of analyte using the following method:

A blood sample is produced by either venipuncture or finger stick. The sample collection/transfer means can be used to collect the sample by simply bringing the sample in contact and then transferring the sample to the test device through an appropriate complementary orifice wherein the sample collected on the collection/transfer means is in direct contact with bibulous material at a specific site along its length and is transferred by diffusion into its pores.

After the sample has been added to the test device at the appropriate position, pressure is applied to a portion of the device compartment to come into contact with the bibulous support. The solvent buffer diffuses along the bibulous support and carries the sample along the bibulous support until it reaches the reaction zone. The buffer carries sample towards the central binding area. As the sample passes over the analyte binding region, the analyte binds to the region. Excess sample and contaminants are rinsed into the absorbant pad.

As the sample is migrating over the first membrane, solvent is migrating over the reaction zone which is the second upper membrane. This solvent solubilizes the detection reagent and carries detection reagent to the central part of the membrane. If analyte is bound to the analyte binding substance in the reaction zone, the detection reagent will bind to the analyte and a visual line will form in the reaction zone.

EXAMPLE

The following example describes a test for the detection of antibody to HIV from fingerstick. In the detection of antibodies to HIV peptides (i.e. gp120) On the opposite side of the surface containing the reaction zone is placed a narrow strip of absorbant which guides the solvent and the sample being transported through the reaction zone thus allowing the anti HIV gp120 antibodies to bind the gp120 antigen previously absorbed and dried in a complementary narrow area on the surface of the porous membrane to create the reaction zone.

In this example, the reaction zone was a 10 mm×10 mm square section of nitrocellulose of 0.45 micron pore size. The zone was coated with 1–2 $\mu$l of a 200 $\mu$l/ml solution of recombinant HIV protein gp120 prepared in a baculovirus system. The sample membrane was nitrocellulose with 5 micron pores as was with detection reagent membrane. The membranes were 10 mm in width and approximately 50 mm in length. All three membranes were blocked by suspension in 0.05 M Tris pH 8.0 for 1 hour then rinsed and dried before being used in the device.

The detection reagent was protein A labeled with gold. This reagent was placed in a solution containing 0.01 M Tris, pH 8.0 containing 0.5% BSA and 1% Trehalose and was adjusted to a concentration such that the O.D. of the final solution was 10. The reagent was dried onto the detection reagent strip.

Solvent buffers for both the sample and the detection reagent strips was 0.01 M phosphate buffered saline, pH 7.4 containing 0.1% Triton X-100.

The test device was able to distinguish negative samples from samples containing HIV antibodies.

We claim:

1. A test strip for use in determining analyte in a test sample, comprising:
    (a) a reservoir consisting essentially of an absorbent pad;
    (b) a reaction zone lying directly above the reservoir comprising an upper surface and a lower surface, a first portion of the upper surface containing analyte binding substance and a second portion lacking the substance, and wherein the lower surface is in physical contact with the reservoir pad;
    (c) an elongated sample zone lying above and in physical contact with a portion of the upper surface of the reaction zone that does not contain analyte binding substance; and
    (d) an elongated detection reagent zone lying above and in physical contact with the portion of the upper surface of the reaction zone that does not contain analyte binding substance,
wherein the sample and detection reagent zones lie opposite each other over the reaction zone with their long axes perpendicular to the physical contact between the lower surface of the reaction zone and the reservoir.

2. The test strip of claim 1, wherein said reaction zone, said sample zone, and said detection reagent zone comprise separate chromatographic materials.

3. The test strip of claim 1 further comprising a water impermeable housing which holds said reservoir, said reaction zone, said sample zone and said detection zone, and wherein the housing comprises an orifice for admission of said test sample.

4. The test strip of claim 3 further comprising a water solution reagent.

5. The test strip of claim 3 further comprising a test sample collecting/transferring device having a size that matches the size of said orifice to allow a surface of said test sample collecting/transferring device to enter said housing.

6. The test strip of claim 5 wherein said test sample collecting/transferring device has a width equal to the width of said sample zone.

7. The test strip of claim 5 wherein said test sample is whole blood.

8. The test strip of claim 7 wherein said test sample collecting/transferring device comprises an absorbent that traps red blood cells.

9. A test strip for use in determining analyte in a test sample, comprising:
    (a) a reservoir consisting essentially of an absorbent pad;
    (b) a reaction zone lying directly above the reservoir comprising an upper surface and a lower surface, a first portion of the reaction zone containing analyte binding substance and a second portion of the reaction zone lacking the binding substance, wherein the lower surface of the first portion but not of the second portion is in physical contact with the reservoir;
    (c) an elongated sample zone lying above and in physical contact with the upper surface of the second portion of the reaction zone; and
    (d) an elongated detection reagent zone lying above and in physical contact with the upper surface of the second portion of the reaction zone,
wherein the sample and detection reagent zones lie opposite each other with their long axes perpendicular to the physical contact between the lower surface of the reaction zone and the reservoir.

10. The test strip of claim 9 wherein said first portion of reaction zone is a narrow line placed perpendicular to said long axes of the sample and detection reagent zones.

11. The test strip of claim 9 further comprising a water solution reagent.

12. The test strip of claim 9 further comprising a water impermeable housing which holds said reservoir, said reaction zone, said sample zone and said detection zone, and wherein the housing comprises an orifice with a size suitable for admitting said test sample within the housing.

13. The test strip of claim 12 further comprising a test sample collecting/transferring device having a size that matches said orifice size to allow a surface of the test sample collecting/transferring device to enter said housing.

14. The test strip of claim 13 wherein said test sample collecting/transferring device has a width equal to the width of said sample zone.

15. The test strip of claim 14, wherein said test sample is whole blood.

16. The test strip of claim 15 wherein said test sample collecting/transferring device comprises an absorbent that traps red blood cells.

* * * * *